United States Patent [19]

Matsuyama et al.

[11] Patent Number: 5,256,552
[45] Date of Patent: Oct. 26, 1993

[54] PROCESS FOR THE PRODUCTION OF OPTICALLY ACTIVE 2-HYDROXY-4-PHENYLBUTYRIC ACID

[75] Inventors: Akinobu Matsuyama; Teruyuki Nikaido; Yoshinori Kobayashi, all of Niigata, Japan

[73] Assignee: Daicel Chemical Industries, Ltd., Japan

[21] Appl. No.: 913,990

[22] Filed: Jul. 17, 1992

Related U.S. Application Data

[63] Continuation of Ser. No. 415,324, Sep. 21, 1989, filed as PCT/JP89/00120, Feb. 7, 1989, abandoned.

[30] Foreign Application Priority Data

Feb. 8, 1988 [JP] Japan .................................. 63-25738
Apr. 28, 1988 [JP] Japan .................................. 63-105893
Apr. 28, 1988 [JP] Japan .................................. 63-105894

[51] Int. Cl.$^5$ .................. C12P 7/42; C12P 41/00; C12R 1/465; C12R 1/245
[52] U.S. Cl. ...................... 435/146; 435/141; 435/280; 435/822; 435/824; 435/830; 435/836; 435/852; 435/854; 435/856; 435/857; 435/853; 435/873; 435/874; 435/885; 435/911; 435/921; 435/930
[58] Field of Search ............... 435/141, 146, 280, 856, 435/822, 824, 830, 836, 852, 853, 857, 873, 874, 885, 911

[56] References Cited

U.S. PATENT DOCUMENTS

| | | |
|---|---|---|
| 4,530,903 | 7/1985 | Leuchtenberger et al. . |
| 4,609,623 | 9/1986 | Leuchtenberger et al, . |
| 4,824,781 | 4/1989 | Hummel et al. . |

FOREIGN PATENT DOCUMENTS

| | | |
|---|---|---|
| 0024547 | 3/1981 | European Pat. Off. . |
| 0137301 | 4/1985 | European Pat. Off. . |
| 0130288 | 9/1985 | European Pat. Off. . |
| 0218863 | 4/1987 | European Pat. Off. . |
| 6335 | 5/1988 | European Pat. Off. . |
| 0347374 | 12/1989 | European Pat. Off. . |
| 62-100286 | 10/1961 | Japan . |
| 60-12975 | 1/1985 | Japan . |
| 62-212329 | 9/1987 | Japan . |
| 63-32480 | 2/1988 | Japan . |
| 63-32493 | 2/1988 | Japan . |

OTHER PUBLICATIONS

Biotech Abs. 85-12678 J601565394 Aug. 1985.
Biotech Abs 90-05694 J02016987 Jan. 1990.
Biotech Abs 89-14981 WO8907147 Aug. 1989.
Biotech Abs. 90-03378 EP-347374 Dec. 1989.
Biquard, Ann. de Chim., 20, 146 (1933).

Primary Examiner—Herbert J. Lilling
Attorney, Agent, or Firm—Birch, Stewart, Kolasch & Birch

[57] ABSTRACT

2-Oxo-4-phenylbutyric acid is treated with a microorganism, which has been optionally treated, capable of asymmetrically reducing 2-oxo-4-phenylbutyric acid into either (R)-2-hydroxy-4-phenylbutyric acid or (S)-2-hydroxy-4-phenylbutyric acid, and the (R)-2-hydroxy-4-phenylbutyric acid or (S)-2-hydroxy-4-phenylbutyric acid thus produced is recovered to thereby give optically active 2-hydroxy-4-phenylbutyric acid.

The optically active 2-hydroxy-4-phenylbutyric acid is an important intermediate in the synthesis of various drugs such as a remedy for hypertension.

9 Claims, No Drawings

PROCESS FOR THE PRODUCTION OF OPTICALLY ACTIVE 2-HYDROXY-4-PHENYLBUTYRIC ACID

This application is a continuation of application Ser. No. 07/415,324 filed on Sep. 21, 1989, filed as PCT/JP89/00120, Feb. 2, 1989, now abandoned.

TECHNICAL FIELD

This invention relates to a process for the production of optically active 2-hydroxy-4-phenylbutyric acid. More particularly, it relates to a process for the production of 2-hydroxy-4-phenylbutyric acid which comprises treating 2-oxo-4-phenylbutyric acid with a microorganism, which has been optionally treated, capable of asymmetrically reducing 2-oxo-4-phenylbutyric acid into either (R)-2-hydroxy-4-phenylbutyric acid or (S)-2-hydroxy-4-phenylbutyric acid and recovering the (R)-2-hydroxy-4-phenylbutyric acid or (S)-2-hydroxy-4-phenylbutyric acid thus formed.

Optically active 2-hydroxy-4-phenylbutyric acid is an important intermediate in the synthesis of various drugs, for example, a remedy for hypertension.

BACKGROUND ART

Known methods for the production of optically active 2-hydroxy-4-phenylbutyric acid include optical resolution of an ester prepared from racemic 2-hydroxy-4-phenylbutyric acid and l-menthol [cf. D. Biquard, Ann. de. Chimie, 20, 146 (1933)] and chemical synthesis from benzylmagnesium chloride and optically active glycidic acid (cf. Japanese Patent Laid-Open No. 212329/1987). However the former method comprising optical resolution is disadvantageous in that the l-menthol is expensive, while latter method comprising the chemical synthesis is disadvantageous in that optically active serine which is the starting material for the preparation of the optically active glycidic acid is expensive for industrial uses.

There have been reported microbial enzymes capable of asymmetrically reducing a 2-oxocarboxylic acid to thereby give an optically active 2-hydroxy carboxylic acid (cf. Japanese Patent Laid-Open No. 12975/1985, Japanese Patent Publication No. 11591/1986, Japanese Patent Laid-Open No. 100286/1987, Japanese Patent Laid-Open No. 32480/1988 and Japanese Patent Laid-Open No. 32493/1988). However, none of these references discloses a process for the production of optically active 2-hydroxy-4-phenylbutyric acid from 2-oxo-4-phenylbutyric acid. Furthermore, no process for the production of optically active 2-hydroxy-4-phenylbutyric acid from 2-oxo-4-phenylbutyric acid by using a microorganism has been reported so far.

DISCLOSURE OF INVENTION

The present inventors have paid attention to a process for conveniently producing optically active 2-hydroxy-4-phenylbutyric acid having a high optical purity through asymmetric reduction with a microorganism, and have attempted to discover microorganisms suitable for the above purpose. As a result, they have found that microorganisms belonging to the genera Lactobacillus, Leuconostoc, Streptococcus, Sporolactobacillus, Pediococcus, Saccharomycopsis, Saccharomyces, Rhodotolura, Candida, Torulaspora, Sporidiobolus, Ambrosiozyma, Arthroascus, Botryoascus, Clavispora, Debaryomyces, Lipomyces, Lodderomyces, Metschnikowia, Geotrichum, Kluyveromyces, Cryptococcus, Trigonopsis, Wickerhamia, Wickerhamiella, Schizosaccharomyces, Rhodosporidium, Stephanoascus, Hansenula, Achromobacter, Bacillus, Escherichia, Micrococcus, Proteus, Serratia, Staphylococcus, Mycobacterium, Brevibacterium, Aureobacterium, Flavobacterium, Salmonella, Erwinia, Agrobacterium, Acetobacter, Paracoccus, Protaminobacter, Pseudomonas and Vibrio could asymmetrically reduce 2-oxo-4-phenylbutyric acid to thereby give (R)-2-hydroxy-4-phenylbutyric acid; and that microorganisms belonging to the genera Pediococcus, Lactobacillus, Streptococcus, Brevibacterium and Corynebacterium could asymmetrically reduce 2-oxo-4-phenylbutyric acid to thereby give (S)-2-hydroxy-4-phenylbutyric acid, thus completing the present invention.

In the present invention, any microorganism belonging to the genus Lactobacillus, Leuconostoc, Streptococcus, Sporolactobacillus, Pediococcus, Saccharomycopsis, Saccharomyces, Rhodotolura, Candida, Saccharomyces, Sporidiobolus, Ambrosiozyma, Arthroascus, Botryoascus, Clavispora, Debaryomyces, Lipomyces, Lodderomyces, Metschnikowia, Geotrichum, Kluyveromyces, Cryptococcus, Trigonopsis, Wickerhamia, Wickerhamiella, Schizosaccharomyces, Rhodosporidium, Stephanoascus, Hansenula, Achromobacter, Bacillus, Escherichia, Micrococcus, Proteus, Serratia, Staphylococcus, Mycobacterium, Brevibacterium, Aureobacterium, Flavobacterium, Salmonella, Erwinia, Agrobacterium, Acetobacter, Paracoccus, Protaminobacter, Pseudomonas or Vibrio and capable of asymmetrically reducing 2-keto-4-phenylbutyric acid to thereby give (R)-2-hydroxy-4-phenylbutyric acid or one belonging to the genus Pediococcus, Lactobacillus, Streptococcus, Brevibacterium or Corynebacterium and capable of asymmetrically reducing 2-oxo-4-phenylbutyric acid to thereby give (S)-2-hydroxy-4-phenylbutyric acid may be used.

Particular examples of the microorganism capable of producing (R)-2-hydroxy-4-phenylbutryic acid from 2-oxo-4-phenylbutyric acid include *Lactobacillus acidophilus* NRIC1027 and IFO3831, *Lactobacillus casei* NRIC1044 and ATCC25598, *Lactobacillus casei* subsp. *rhamnosus* IFO3425, *Lactobacillus casei* subsp. *casei* IFO12004, *Lactobacillus delbrueckii* AHU1056, *Lactobacillus brevis* NRIC1037 and ATCC4006, *Lactobacillus bulgaricus* NRIC1041 and IAM1120, *Lactobacillus fructosus* IFO3516, *Lactobacillus lactis* NRIC1061 and ATCC12315, *Lactobacillus xylosus* NRIC1074 and ATCC15577, *Lactobacillus leichmannii* AHU1681, *Lactobacillus virideescens* NRIC1073 and ATCC12706, *Leuconostoc dextranicum* AHU1080, *Leuconostoc destranicum* ATCC17072, *Leuconostoc mesenteroides* AHU1067, *Leuconostoc mesenteroides* subsp. *dextranicum* IFO3349, *Leuconostoc mesenteroides* subsp. *mesenteroides* IFO3426, *Lueconostoc citrovorum* NRIC1089, *Streptococcus faecalis* IFO12964, *Streptococcus faecium* NRIC1145 and ATCC19434, *Sterptococcus* sp. IFO3427, *Streptococcus* sp. IFO3535, *Streptococcus lactis* AHU1089, *Streptococcus uberis* NRIC1153 and ATCC19436, *Sporolactobacillus inulinus* NRIC1133 and ATCC15538, *Pediococcus acidilactici* NRIC1102 and ATCC8081, *Saccharomycopsis fibuligera* IFO0103, *Saccharomycopsis lipolytica* IFO1550, *Saccharomyces bayanus* IFO0262, *Saccharomyces kluyveri* KF01894, *Saccharomyces uvarum* IFO0565, *Saccharomyces chevalieri* IFO0222, *Rhodotolura glutinis* AHU3942, *Candida humicola* IFO0760, *Candida parapsilosis* IFO1396, *Candida rugosa* IFO0750, *Torulaspora delbruekii* IFO0955,

*Sporidiobolus johnsonii* IFO6903, *Ambrosiozyma cicatricosa* IFO1846, *Ambrosiozyma platypodis* IFO1471, *Arthroascus javanensis* IFO1848, *Botryoassus synnaedendrus* IFO1604, *Clavispora lusitanias* IFO1019, *Debaryomyces hansenii* IFO0083, *Lipomyces starkeyi* IFO1289, *Lodderomyces elongisporus* IFO1676, *Metschnikowia bicuspidata* IFO1408, *Geotrichum candidum* IFO4601, *Kluyveromyces lactis* IFO1903, *Cryptococcus neoformans* IAM4788, *Trigonopsis variabilis* IFO0755, *Wickerhamia fluorescens* IFO1116, *Wickerhamiella domercquii* IFO1857, *Schizosaccharomyces octosporus* IFO0353, *Rhodosporidium dibovatum* IFO1829, *Stephanoascus ciferrii* IFO1854, *Hansenula fabianii* IFO1253, *Achromobacter pestifer* ATCC23584, *Bacillus licheniformis* IFO12200, *Escherichia coli* IFO3544, *Micrococcus luteus* IFO12992, *Proteus vulgaris* IFO3167, *Serratia marcescens* IAM12143, *Staphylococcus aureus* IFO3060, *Mycobacterium smegmatis* IFO3153, *Brevibacterium iodinum* IFO3558, *Aureobacterium testaceum* IFO12675, *Flavobacterium suaveolens* IFO3752, *Salmonella typhimurium* IFO12529, *Erwinia carotovora* IFO3830, *Agrobacterium radiobacter* IFO12664, *Acetobacter pasteurianus* ATCC10245, *Paracoccus denitrificans* IFO12442, *Protaminobacter ruber* IAM9081, *Pseudomonas aureofaciens* IFO3522 and *Vibrio anguillarum* IFO12710.

Examples of the microorganism capable of producing (S)-2-hydroxy-4-phenylbutyric acid from 2-oxo-4-phenylbutyric acid include *Pediococcus pentosaceus* IFO3891, *Lactobacillus plantarum* IFO3070, *Streptococcus agalactiae* NRIC1137 and ATCC13813, *Streptococcus lactis* NRIC1149 and ATCC19435, *Brevibacterium ammoniagenes* IAM1641 and *Corynebacterium glutamicum* ATCC13032.

Each strain may be either a wild type, a variant, or a recombinant obtained by genetic engineering such as by cell fusion or gene recombination.

Microorganisms having IFO numbers assigned thereto are described in the List of Culture, 8th ed., vol. 1 (1988) published by the Institute for Fermentation, 17-85 Jusohomachi, 2-chome, Yodogawa-ku, Osaka 532, Japan (IFO) and are available therefrom. *Leuconostoc mesenteroides* subspecies *dextranicum*, IFO 3349 was deposited on Nov. 1, 1954. *Lactobacillus paracasei* subspecies *paracasei* (*Lactobacillus casei*), IFO 12004 was deposited on Mar. 3, 1963. Those having AHU numbers are described in the Catalogue Culture, 4th ed. (1987) published by Japan Federation of Culture Collection (JFCC) and are available from the Faculty of Agriculture, Hokkaido University. Those having ATCC numbers are described in the Catalogue of Bacteria Phages rDNA Vectors, 16th ed. (1985) published by American Type Culture Collection (ATCC) and are available therefrom. Those having NRIC numbers are described in the Culture Collection of NODAI No. 1 (1985) published by Tokyo University of Agriculture and are available therefrom. Those having IAM numbers are available from the Institute of Applied Microbiology, the University of Tokyo.

The microorganism to be used in the present invention may be cultured in any medium so long as it can grow therein. Any carbon source may be used so long as said microorganism can utilize it. Examples thereof include sugars such as glucose, fructose, sucrose and dextrin, alcohols such as sorbitol, ethanol and glycerol, organic acids such as fumaric, citric, acetic and propionic acids and salts thereof, and hydrocarbons such as paraffin and mixtures thereof. Examples of a nitrogen source include ammonium salts of inorganic acids, such as ammonium chloride, ammonium sulfate and ammonium phosphate, ammonium salts of organic acids, such as ammonium fumarate and ammonium citrate, nitrogenous materials such as meat extract, yeast extract, corn steep liquor, casein hydrolysate and urea and mixtures thereof. Furthermore, various nutritional sources commonly used in the culture of microorganisms, such as inorganic salts, trace metal salts and vitamins, may be appropriately mixed and used in the present invention. In addition, materials effective in promoting the growth of the microorganism, in elevating the productivity of the target compound, or in maintaining the pH value of the medium at the desired level may be added, if required.

The pH value of the medium may be adjusted to 3.0 to 9.5, preferably 4 to 8. Culturing may be carried out at a temperature of 20° to 45° C., preferably 25° to 37° C., either aerobically or anaerobically under conditions suitable for the growth of the microorganism, for 15 to 120 hours, preferably 12 to 72 hours.

The reduction may be effected by using the culture medium as such. Alternately, the cells may be separated by, for example, centrifugation, optionally washed, and resuspended in a buffer solution or water. 2-oxo-4-phenylbutyric acid may be added to the suspension thus obtained. In this reaction, it is sometimes preferable to add a carbon source such as glucose or sucrose to the medium to thereby supply energy. The cells may be used as such in the form of viable cells. Alternately, they may be ground, treated with acetone, or lyophilized. These cells, which have been optionally treated, may be immobilized prior to use by a conventional method employing polyacrylamide gel, carrageenan gel, alginic acid gel or agar gel. Furthermore, an enzyme obtained from said treated cells by combining known methods may be used in the present invention.

The 2-oxo-4-phenylbutyric acid may be added either at once at the initiation of the reaction or by portions either as such, dissolved in water or an inert organic solvent, or dispersed in, for example, a surfactant. The 2-oxo-4-phenylbutyric acid may be used in the form of various salts such as ammonium, sodium, calcium or potassium salt.

The reaction may be conducted at a pH value of 3 to 9, preferably 5 to 8, at 10° to 60° C., preferably 20° to 40° C. for 1 to 120 hours with or without stirring. The concentration of the substrate may preferably range from 0.1 to 10%, though it is not restricted thereby.

The optically active 2-hydroxy-4-phenylbutyric acid thus formed may be readily collected by extracting the reaction mixture, from which the cells may be optionally separated, with an organic solvent and purifying the extract by, for example, column chromatography or recrystallization.

BEST MODE FOR CARRYING OUT THE INVENTION

To further illustrate the present invention, and not by way of limitation, the following Examples will be given.

In each Example, the absolute configuration and optical purity were determined by extracting the reaction product with ethyl acetate, ethyl-esterifying the same in a conventional manner, and subjecting the obtained ester to high performance liquid chromatography by using an optical resolution column [column: Chiral cell OB, mfd. by Daicel Chemical Industries, Ltd., 4.6 mm (i.d.)×250 mm, solvent: n-hexane: 2-propanpol (19:1 v/v), flow rate: 0.5 ml/min, Detection:

254 nm]. The reaction yield was determined by high performance liquid chromatography by using a reverse phase column [column: Nucleosil 10C18, 4.0 mm (i.d.)×250 mm, solvent: 40 mM phosphate buffer (pH 3.0)/acetonitrile=4:1, flow rate: 1 ml/min, detection: 254 nm].

EXAMPLE 1

100 ml of a medium comprising 2% of glucose, 0.5% of yeast extract, 0.5% of peptone, 0.5% of meat extract, 0.2% of dipotassium phosphate and 1% of calcium carbonate was introduced into a 500-ml Erlenmeyer flask and sterilized. Next, each strain specified in Table 1 was inoculated thereto and cultured therein at 30° C. for 30 hours under shaking.

After the completion of culturing, the cells were separated by centrifugation and washed once with a physiological saline solution to thereby yield viable cells.

7.5 ml of distilled water was introduced into a 100-ml Erlenmeyer flask and the above viable cells were suspended therein. 1.2 g of glucose was added to the suspension thus obtained and the resulting mixture was shaken under rotation at 30° for 10 minutes. Then 2.5 ml of a 4% aqueous solution of 2-oxo-4-phenylbutyric acid, with the pH value adjusted to 7 with caustic potash, and 0.3 g of calcium carbonate were added thereto and the resulting mixture was shaken under rotation at 30° C. for 40 hours.

After the completion of the reaction, sulfuric acid was added to the reaction mixture to thereby adjust the pH value thereof to 1 or below. Then the optically active 2-hydroxy-4-phenylbutyric acid thus formed was extracted with 20 ml of ethyl acetate. The yield was determined by removing a given amount of the solvent from the ethyl acetate phase under reduced pressure, dissolving the residue thus obtained in the abovementioned eluent, and determining the amount of 2-hydroxy-4-phenylbutyric acid thus formed by high performance liquid chromatography by using a reverse phase column.

Similarly, a given amount of the solvent was removed from the ethyl acetate phase under reduced pressure and the residue was ethyl-esterified in a conventional manner. Then the absolute configuration and optical purity of the 2-hydroxy-4-phenylbutyric acid thus formed was determined by high performance liquid chromatography by using an optical resolution column.

Table 1 shows the results.

EXAMPLE 2

100 ml of a YM medium comprising 0.3% of yeast extract, 0.3% of malt extract, 0.5% of peptone and 2% of glucose (pH 6.0) was introduced into a 500-ml Sakaguchi flask and sterilized. Then each strain specified in Table 2 was inoculated thereto and cultured therein at 30° C. for 48 hours under shaking.

After the completion of the culture, the cells were separated by centrifugation and washed once with a physiological saline solution to thereby yield viable cells.

7.5 ml of distilled water was introduced into a 100-ml Erlenmeyer flask and the abovementioned viable cells were suspended therein. Then 1.2 g of sucrose was added to the obtained suspension and the mixture was reciprocally shaken at 30° C. for 10 minutes. Next, 2.5 ml of a 4% aqueous solution of 2-oxo-4-phenylbutyric acid, with the pH value adjusted to 7 with caustic potash, was added thereto and the resulting mixture was shaken under rotation at 30° C. for 20 hours.

After the completion of the reaction, the reaction mixture was treated in the same manner as the one described in Example 1. Thus the reaction yield and optical purity of the product were determined.

Table 2 shows the results.

EXAMPLE 3

Each microorganism specified in Table 3 was subjected to the same treatment as that described in Example 1, except that the medium contained no calcium carbonate and had a pH value of 7, and the culture was reciprocally conducted in a 500-ml Sakaguchi flask.

Table 3 shows the results.

EXAMPLE 4

*Leuconostoc mesenteroides* subsp. *dextranicum* IFO3349 was inoculated into 2-l of the same medium as the one described in Example 1 in a 5-l jar fermenter and cultured therein at 30° C. under stirring at 100 rpm for 30 hours.

After the completion of the culture, the cells were collected by centrifugation and washed with 1-l of water. Then these cells were suspended in 400 ml of water. Then these cells were suspended in 400 ml of water and introduced into a 2-l Erlenmeyer flask. 50 ml of a 10% aqueous solution of 2-oxo-4-phenylbutyric acid, with the pH value adjusted to 7 with caustic potash, 40 g of glucose and 4 g of calcium carbonate were added thereto and the obtained mixture was allowed to react at 30° C. under stirring for 72 hours.

After the completion of the reaction, the pH value of the reaction mixture was adjusted to 1.5 with conc. sulfuric acid. The (R)-2-hydroxy-4-phenylbutyric acid thus formed was extracted with 200-ml portions of ethyl acetate twice. The ethyl acetate phase was dehydrated with anhydrous Glauber's salt and the solvent was removed under reduced pressure to thereby give 4.5 g of crude crystals. These crystals were recrystallized from toluene to thereby give 3.6 g of the desired (R)-2-hydroxy-4-phenylbutyric acid in the form of crystals (yield: 72%, optical purity: 99% e.e.).

EXAMPLE 5

*Wickerhamiella domercquii* IFO1957 was inoculated into 2-l of the same medium as the one described in Example 3 in a 5-l jar fermenter and cultured therein at 30° C. under stirring at 400 rpm and aerating at 1 vvm for 30 hours.

After the completion of culturing, the cells were collected by centrifugation and washed with 1-l of water. Then these cells were suspended in 200 ml of water and introduced into a 1-l Erlenmeyer flask. 20 ml of a 10% aqueous solution of 2-oxo-4-phenylbutyric acid, with the pH value adjusted to 7 with caustic potash, and 20 g of glucose were added thereto and the obtained mixture was allowed to react at 30° C. under stirring for 24 hours.

After the completion of the reaction, the reaction mixture was treated in the same manner as the one described in Example 4. Thus 1.2 g of the desired (R)-2-hydroxy-4-phenylbutyric acid was obtained in the form of crystals (yield: 60%, optical purity: 99% e.e.).

EXAMPLE 6

*Flavobacterium suaveolens* IFO3752 was inoculated into 2-l of the same medium as the one described in Example 3 in a 5-l jar fermenter and cultured therein at 30° C. under stirring at 400 rpm and aerating at 1 vvm for 30 hours.

After the completion of culturing, the cells were collected by centrifugation and washed with 1-l of water. Then these cells were suspended in 400 ml of water and introduced into a 2-l Erlenmeyer flask. 50 ml of a 10% aqueous solution of 2-oxo-4-phenylbutyric acid, with the pH value adjusted to 7 with caustic potash, and 40 g of glucose were added thereto and the obtained mixture was allowed to react at 30° C. under stirring for 72 hours.

After the completion of the reaction, the reaction mixture was treated in the same manner as the one described in Example 4. Thus 2.3 g of crude crystals of the desired (R)-2-hydroxy-4-phenylbutyric acid were obtained. After recrystallization from toluene, 1.8 g of the aimed (R)-2-hydroxy-4-phenylbutyric acid was obtained in the form of crystals (yield: 36%, optical purity: 99% e.e.).

EXAMPLE 7

Streptococcus agalactiae NRIC1137 was inoculated into 2-l of the same medium as the one described in Example 3 in a 5-l jar fermenter and cultured therein at 30° C. under stirring at 100 rpm for 30 hours.

After the completion of the culture, the cells were collected by centrifugation and washed with 1-l of water. Then these cells were suspended in 200 ml of water and introduced into a 1-l Erlenmeyer flask. 25 ml of a 10% aqueous solution of 2-oxo-4-phenylbutyric acid, with the pH value adjusted to 7 with caustic potash, 20 g of glucose and 2 g of calcium carbonate were added thereto and the obtained mixture was allowed to react at 30° C. under stirring for 24 hours.

After the completion of the reaction, the reaction mixture was treated in the same manner as the one described in Example 4. Thus 1.4 g of crude crystals of the desired (S)-2-hydroxy-4-phenylbutyric acid was obtained. After recrystallization from toluene, 1.1 g of the desired (S)-2-hydroxy-4-phenylbutyric acid was obtained in the form of crystals (yield: 44%, optical purity: 98% e.e.).

The process of the present invention for the production of optically active 2-hydroxy-4-phenylbutyric acid through asymmetric reduction by using a microorganism makes it possible to readily produce optically active 2-hydroxy-4-phenylbutyric acid having a high optical purity. Thus it is highly advantageous as an industrial process.

TABLE 1

| Microorganism | Yield (%) | Optically active 2-hydroxy-4-phenylbutyric acid Absolute configuration | Optical purity (% e.e.) |
|---|---|---|---|
| Lactobacillus acidophilus NRIC1027 | 16 | R | 30 |
| Lactobacillus casei NRIC1044 | 20 | R | 81 |
| Lactobacillus casei subsp. rhamnosus IFO3425 | 30 | R | 45 |
| Lactobacillus casei subsp. casei IFO12004 | 11 | R | 100 |
| Lactobacillus delbrueckii AHU1056 | 41 | R | 56 |
| Lactobacillus brevis NRIC1037 | 11 | R | 73 |
| Lactobacillus bulgaricus NRIC1041 | 14 | R | 100 |
| Lactobacillus fructosus IFO3516 | 34 | R | 100 |
| Lactobacillus lactis NRIC1061 | 33 | R | 56 |
| Lactobacillus xylosus NRIC1074 | 21 | R | 70 |
| Lactobacillus leichmanii AHU1681 | 14 | R | 100 |
| Lactobacillus viridescens NRIC1073 | 19 | R | 84 |
| Leuconostoc dextranicum AHU1080 | 99 | R | 45 |
| Leuconostoc dextranicum ATCC17072 | 40 | R | 100 |
| Leuconostoc mesenteroides AHU1067 | 91 | R | 100 |
| Leuconostoc mesenteroides subsp. dextranicum IFO3349 | 95 | R | 100 |
| Leuconostoc mesenteroides subsp. mesenteroides IFO3426 | 43 | R | 36 |
| Leuconostoc citrovorum NRIC1089 | 8 | R | 65 |
| Streptococcus faecalis IFO12964 | 63 | R | 43 |
| Streptococcus faecium NRIC1145 | 11 | R | 49 |
| Streptococcus sp. IFO3427 | 39 | R | 71 |
| Streptococcus sp. IFO3535 | 54 | R | 83 |
| Streptococcus lactis AHU1089 | 47 | R | 21 |
| Streptococcus uberis NRIC1153 | 17 | R | 34 |
| Sporolactobacillus inulinus NRIC1133 | 17 | R | 91 |
| Pediococcus acidilactici NRIC1102 | 17 | R | 73 |
| Pediococcus pentosaceus IFO3891 | 13 | S | 70 |
| Lactobacillus plantarum IFO3070 | 71 | S | 52 |
| Streptococcus agalactiae NRIC1137 | 42 | S | 100 |
| Streptococcus lactis NRIC1149 | 13 | S | 41 |

TABLE 2

| Microorganism | Yield (%) | Optically active 2-hydroxy-4-phenylbutyric acid Absolute configuration | Optical purity (% e.e.) |
|---|---|---|---|
| Saccharomycopsis fibuligera IFO0103 | 22 | R | 100 |
| Saccharomycopsis lipolytica IFO1550 | 18 | R | 82 |
| Saccharomyces bayanus IFO0262 | 13 | R | 53 |
| Saccharomyces kluyveri IFO1894 | 15 | R | 46 |
| Saccharomyces uvarum IFO0565 | 12 | R | 34 |
| Saccharomyces chevalieri IFO0222 | 10 | R | 24 |
| Rhodotolura glutinis AHU3942 | 19 | R | 100 |
| Candida humicola IFO0760 | 39 | R | 100 |

TABLE 2-continued

| Microorganism | Yield (%) | Absolute configuration | Optical purity (% e.e.) |
|---|---|---|---|
| Candida parapsilosis IFO1396 | 16 | R | 92 |
| Candida rugosa IFO0750 | 7 | R | 31 |
| Torulaspora delbruekii IFO0955 | 16 | R | 100 |
| Sporidiobolus johnsonii IFO6903 | 35 | R | 100 |
| Ambrosiozyma cicatricosa IFO1846 | 15 | R | 100 |
| Ambrosiozyma platypodis IFO1471 | 13 | R | 100 |
| Arthroascus javanensis IFO1848 | 14 | R | 100 |
| Botryoascus synnaedendrus IFO1604 | 16 | R | 100 |
| Clavispora lusitanias IFO1019 | 15 | R | 100 |
| Debaryomyces hansenii IFO0083 | 13 | R | 100 |
| Lipomyces starkeyi IFO1289 | 30 | R | 100 |
| Lodderomyces elongisporus IFO1676 | 29 | R | 100 |
| Metschnikowia bicuspidata IFO1408 | 17 | R | 100 |
| Geotrichum candidum IFO4601 | 21 | R | 100 |
| Kluyveromyces lactis IFO1903 | 11 | R | 100 |
| Cryptococcus neoformans IAM4788 | 30 | R | 100 |
| Trigonopsis variabilis IFO0755 | 17 | R | 100 |
| Wickerhamia fluorescens IFO1116 | 16 | R | 100 |
| Wickerhamiella domercquii IFO1857 | 51 | R | 100 |
| Schizosaccharomyces octosporus IFO0353 | 51 | R | 100 |
| Rhodosporidium diobovatum IFO1829 | 37 | R | 100 |
| Stephanoascus ciferii IFO1854 | 13 | R | 100 |
| Hansenula fabianii IFO1253 | 13 | R | 100 |

TABLE 3

| Microorganism | Yield (%) | Absolute configuration | Optical purity (% e.e.) |
|---|---|---|---|
| Achromobacter pestifer ATCC23584 | 13 | R | 100 |
| Bacillus licheniformis IFO12200 | 18 | R | 100 |
| Escherichia coli IFO3544 | 13 | R | 100 |
| Micrococcus luteus IFO12992 | 13 | R | 100 |
| Proteus vulgaris IFO3167 | 20 | R | 89 |
| Serratia marcescens IAM12143 | 40 | R | 94 |
| Stapylococcus aureus IFO3060 | 19 | R | 100 |
| Mycobacterium smegmatis IFO3153 | 39 | R | 100 |
| Brevibacterium iodinum IFO3558 | 32 | R | 49 |
| Aureobacterium testaceum IFO12675 | 14 | R | 100 |
| Flavobacterium suaveolens IFO3752 | 32 | R | 100 |
| Salmonella typhimurium IFO2529 | 14 | R | 100 |
| Erwinia carotovora IFO3830 | 19 | R | 100 |
| Agrobacterium radiobacter IFO12664 | 13 | R | 100 |
| Acetobacter pasteurianus ATCC10245 | 12 | R | 100 |
| Paracoccus denitrificans IFO12442 | 21 | R | 100 |
| Protaminobacter ruber IAM9081 | 19 | R | 100 |
| Pseudomonas aureofaciens IFO3522 | 11 | R | 100 |
| Vibrio anguillarum IFO12710 | 10 | R | 20 |
| Brevibacterium ammoniagenes IAM1641 | 23 | S | 49 |
| Corynebacterium glutamicum ATCC13032 | 24 | S | 10 |

We claim:

1. A process for the production of optically active 2-hydroxy-4-phenylbutyric acid which comprises treating 2-oxo-4-phenylbutyric acid with a microorganism, which has been optionally treated, capable of asymmetrically reducing 2-oxo-4-phenylbutyric acid into either (R)-2-hydroxy-4-phenylbutyric acid or (S)-2-hydroxy-4-phenylbutyric acid, said treatment of 2-oxo-4-phenylbutyric acid being conducted in a medium containing as a source of nitrogen at least one of the substances selected from the group consisting of ammonium salts of inorganic acids, ammonium fumarate, ammonium citrate, ammonium salts of an organic acid, meat extract, yeast extract, corn steep liquor, casein hydrolysate, and urea, and collecting the (R)-2-hydroxy-4-phenylbutyric acid or (S)-2-hydroxy-4-phenylbutyric acid thus formed.

2. A process as claimed in claim 1, wherein said microorganism capable of producing (R)-2-hydroxy-4-phenylbutyric acid is selected from the group consisting the genera Lactobacillus, Leuconostoc, Streptococcus, Sporolactobacillus, Pediococcus, Saccharomycopsis, Saccharomyces, Rhodotolura, Candida, Torulaspora, Sporidiobolus, Ambrosiozyma, Arthroascus, Botryoascus, Clavispora, Debaryomyces, Lipomyces, Lodderomyces, Metschnikowia, Geotrichum, Kluyveromyces, Cryptococcus, Trigonopsis, Wickerhamia, Wickerhamiella, Schizosaccharomyces, Rhodosporidium, Stephanoascus, Hansenula, Achromobacter, Bacillus, Escherichia, Micrococcus, Proteus, Serratia, Staphylococcus, Mycobacterium, Brevibacterium, Aureobacterium, Flavobacterium, Salmonella, Erwinia, Agrobacterium, Acetobacter, Paracoccus, Protaminobacter, Pseudomonas and Vibrio.

3. A process as claimed in claim 1, wherein said microorganism capable of producing (S)-2-hydroxy-4-phenylbutyric acid is selected from the group consisting of the genera Pediococcus, Lactobacillus, Streptococcus, Brevibacterium and Corynebacterium.

4. A process as claimed in claim 1, which comprises using a microorganism, which has been optionally treated, selected from the group consisting of the genera Lactobacillus, Leuconostoc, Streptococcus, Saccharomycopsis, Rhodotolura, Candida, Saccharomyces and Sporidiobolus.

5. A process as claimed in claim 1, which comprises using a microorganism, which has been optionally treated, selected from the group consisting of the genera Spororactobacillus, Achromobacter, Bacillus, Escherichia, Micrococcus, Proteus, Serratia, Staphylococcus, Micobacterium, Chromobacterium, Aureobacterium, Flavobacterium, Salmonella, Erwinia, Agrobacterium, Acetobacter, Paracoccus, Protaminobacter, Pseudomonas, Ambrosiozyma, Arthroascus, Botyoascus, Clavispora, Debaryomyces, Lipomyces, Lodderomyces, Metschnikowia, Geotrichum, Kluyveromyces, Cryptococcus, Trigonopsis, Wickerhamia, Wickerhamiella, Schizosaccharomyces, Rhodosporidium, Stephanoascus and Hansenula and capable of asymmetrically reducing 2-keto-4-phenylbutyric acid into (R)-2-hydroxy-4-phenylbutyric acid.

6. A process as claimed in claim 1, wherein said optionally treated microorganism has been ground, treated with acetone, or lyophilized.

7. A process as claimed in claim 6, wherein said cells which have been optionally treated are immobilized.

8. A process as claimed in claim 2, wherein said microorganism is selected from the group consisting of *Lactobacillus casei* subsp. casei IFO 12004 and *Leuconostoc mesenteroides* subsp. dextranicum IFO 3349.

9. A process for the production of optically active 2-hydroxy-4-phenylbutyric acid which comprises treating 2-oxo-4-phenylbutyric acid with a microorganism, which has been optionally treated, capable of asymmetrically reducing 2-oxo-4-phenylbutyric acid into either (R)-2-hydroxy-4-phenylbutyric acid or (S)-2-hydroxy-4-phenylbutyric acid, said treatment of 2-oxo-4-phenylbutyric acid to occur in a medium consisting essentially of water, a buffer to maintain the pH value between 3 and 9 and a carbon source selected from the group consisting of glucose and sucrose and collecting the (R)-2-hydroxy-4-phenylbutyric acid or (S)-2-hydroxy-4-phenylbutyric acid thus formed.

* * * * *